US011071869B2

(12) United States Patent
Leigh et al.

(10) Patent No.: US 11,071,869 B2
(45) Date of Patent: Jul. 27, 2021

(54) IMPLANTABLE DEVICE HAVING REMOVABLE PORTION

(71) Applicant: Cochlear Limited, Macquarie University (AU)

(72) Inventors: Charles Roger Leigh, Macquarie University (AU); Padraig Hurley, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 186 days.

(21) Appl. No.: 15/336,662

(22) Filed: Oct. 27, 2016

(65) Prior Publication Data

US 2017/0239474 A1 Aug. 24, 2017

Related U.S. Application Data

(60) Provisional application No. 62/299,467, filed on Feb. 24, 2016.

(51) Int. Cl.
*A61N 1/375* (2006.01)
*A61N 1/372* (2006.01)
*A61N 1/36* (2006.01)
*A61N 1/08* (2006.01)
*A61N 1/37* (2006.01)

(52) U.S. Cl.
CPC ......... *A61N 1/375* (2013.01); *A61N 1/36038* (2017.08); *A61N 1/37223* (2013.01); *A61N 1/08* (2013.01); *A61N 1/3718* (2013.01); *A61N 1/37229* (2013.01)

(58) Field of Classification Search
CPC . A61N 1/36036; A61N 1/37223; A61N 1/375
See application file for complete search history.

(56) References Cited

U.S. PATENT DOCUMENTS

| | | | |
|---|---|---|---|
| 3,244,174 | A | 4/1966 | Wesbey et al. |
| 3,875,349 | A | 4/1975 | Ruegg |
| 4,388,523 | A | 6/1983 | Keep, Jr. et al. |
| 4,443,666 | A | 4/1984 | Cote |
| 4,450,930 | A | 5/1984 | Killion |
| 4,504,703 | A | 3/1985 | Schneiter et al. |

(Continued)

FOREIGN PATENT DOCUMENTS

| | | |
|---|---|---|
| WO | WO2001074447 | 10/2001 |
| WO | 200191678 A1 | 12/2001 |

(Continued)

OTHER PUBLICATIONS

Bal Seal® Engineering, Inc., "Sealing, Connecting Conducting and Shielding Solutions for Healthcare," 8 pages, 2013.

(Continued)

*Primary Examiner* — William J Levicky
(74) *Attorney, Agent, or Firm* — Pilloff Passino & Cosenza LLP; Martin J. Cosenza

(57) ABSTRACT

Medical devices allow for the complete removal of a portion of an implantable component that contains a magnet. Such structure allows a recipient to undergo MRI procedures without interference from the implanted magnet. The magnet can also be contained within a larger, non-magnetic chassis that acts as an enlarged lever arm having a greater torque resistance against the generated magnetic forces.

19 Claims, 12 Drawing Sheets

(56) References Cited

U.S. PATENT DOCUMENTS

| | | |
|---|---|---|
| 4,532,930 A | 8/1985 | Crosby et al. |
| 4,606,329 A | 8/1986 | Hough |
| 4,607,383 A | 8/1986 | Ingalls |
| 4,621,171 A | 11/1986 | Wada et al. |
| 4,744,370 A | 5/1988 | Harris |
| 4,774,933 A | 10/1988 | Hough et al. |
| 4,815,560 A | 3/1989 | Madaffari |
| 4,837,833 A | 6/1989 | Madaffari |
| RE33,170 E | 2/1990 | Byers |
| 4,932,405 A | 6/1990 | Peeters et al. |
| 4,936,305 A | 6/1990 | Ashtiani et al. |
| 4,961,434 A | 10/1990 | Stypulkowski |
| 5,000,194 A | 3/1991 | Van Den Homert et al. |
| 5,015,224 A | 5/1991 | Maniglia |
| 5,042,084 A | 8/1991 | Daly |
| 5,105,811 A | 4/1992 | Kuzma |
| 5,163,957 A | 11/1992 | Sadé et al. |
| 5,176,620 A | 1/1993 | Gilman |
| 5,276,739 A | 1/1994 | Krokstad et al. |
| 5,277,694 A | 1/1994 | Leysieffer et al. |
| 5,363,452 A | 11/1994 | Anderson |
| 5,411,467 A | 5/1995 | Hortmann et al. |
| 5,443,493 A | 8/1995 | Byers et al. |
| 5,456,654 A | 10/1995 | Ball |
| 5,507,303 A | 4/1996 | Kuzma |
| 5,522,865 A | 6/1996 | Schulman et al. |
| 5,531,774 A | 7/1996 | Schulman et al. |
| 5,549,658 A | 8/1996 | Shannon et al. |
| 5,554,096 A | 9/1996 | Ball |
| 5,558,618 A | 9/1996 | Maniglia |
| 5,571,148 A | 11/1996 | Loeb et al. |
| 5,578,084 A | 11/1996 | Kuzma et al. |
| 5,613,935 A | 3/1997 | Jarvik |
| 5,624,376 A | 4/1997 | Ball et al. |
| 5,649,970 A | 7/1997 | Loeb et al. |
| 5,653,742 A | 8/1997 | Parker et al. |
| 5,674,264 A | 10/1997 | Carter et al. |
| 5,702,431 A | 12/1997 | Wang et al. |
| 5,720,099 A | 2/1998 | Parker et al. |
| 5,755,743 A | 5/1998 | Volz et al. |
| 5,755,747 A | 5/1998 | Daly et al. |
| 5,824,022 A | 10/1998 | Zilberman et al. |
| 5,876,429 A | 3/1999 | Schreoppel |
| 5,876,443 A | 3/1999 | Hochmair et al. |
| 5,897,486 A | 4/1999 | Ball et al. |
| 5,922,017 A | 7/1999 | Bredberg et al. |
| 5,957,958 A | 9/1999 | Schulman et al. |
| 5,999,859 A | 12/1999 | Jolly |
| 6,074,422 A | 1/2000 | Berrang et al. |
| 6,035,237 A | 3/2000 | Schulman et al. |
| 6,039,685 A | 3/2000 | Bushek |
| 6,067,474 A | 5/2000 | Schulman |
| 6,068,652 A | 5/2000 | Cohen et al. |
| 6,070,105 A | 5/2000 | Kuzma |
| 6,078,841 A | 6/2000 | Kuzma |
| 6,119,044 A | 9/2000 | Kuzma |
| 6,125,302 A | 9/2000 | Kuzma |
| 6,129,753 A | 10/2000 | Kuzma |
| 6,144,883 A | 11/2000 | Kuzma |
| 6,151,400 A | 11/2000 | Seligman |
| 6,157,861 A | 12/2000 | Faltys et al. |
| 6,163,729 A | 12/2000 | Kuzma |
| 6,190,305 B1 | 2/2001 | Ball et al. |
| 6,219,580 B1 | 4/2001 | Faltys et al. |
| 6,259,951 B1 | 7/2001 | Kuzma et al. |
| 6,266,568 B1 | 7/2001 | Mann et al. |
| 6,272,382 B1 | 8/2001 | Faltys et al. |
| 6,289,246 B1 | 9/2001 | Money |
| 6,293,903 B1 | 9/2001 | Kasic, II et al. |
| 6,301,505 B1 | 10/2001 | Money |
| 6,304,787 B1 | 10/2001 | Kuzma et al. |
| 6,308,101 B1 | 10/2001 | Faltys et al. |
| 6,321,125 B1 | 11/2001 | Kuzma |
| 6,321,126 B1 | 11/2001 | Kuzma |
| 6,325,755 B1 | 12/2001 | Bushek et al. |
| 6,355,064 B1 | 3/2002 | Peeters et al. |
| 6,358,281 B1 | 3/2002 | Berrang et al. |
| 6,374,143 B1 | 4/2002 | Berrang et al. |
| 6,397,110 B1 | 5/2002 | Kuzma |
| 6,411,855 B1 | 6/2002 | Peeters et al. |
| 6,421,569 B1 | 7/2002 | Treaba et al. |
| 6,482,144 B1 | 11/2002 | Müller |
| 6,498,954 B1 | 12/2002 | Kuzma et al. |
| 6,517,476 B1 | 2/2003 | Bedoya et al. |
| 6,542,777 B1 | 4/2003 | Griffith et al. |
| 6,554,761 B1 | 4/2003 | Puria et al. |
| 6,556,870 B2 | 4/2003 | Zierhofer et al. |
| 6,565,503 B2 | 5/2003 | Leysieffer et al. |
| 6,572,531 B2 | 6/2003 | Zilberman et al. |
| 6,592,512 B2 | 7/2003 | Stockert et al. |
| 6,600,955 B1 | 7/2003 | Zierhofer |
| 6,604,283 B1 | 8/2003 | Kuzma |
| 6,620,094 B2 | 9/2003 | Miller |
| 6,629,923 B2 | 10/2003 | Leysieffer |
| 6,648,914 B2 | 11/2003 | Berrang et al. |
| 6,697,674 B2 | 2/2004 | Leysieffer |
| 6,736,770 B2 | 5/2004 | Leysieffer et al. |
| 6,757,970 B1 | 7/2004 | Kuzma et al. |
| 6,778,858 B1 | 8/2004 | Peeters |
| 6,786,860 B2 | 9/2004 | Maltan et al. |
| 6,807,445 B2 | 10/2004 | Baumann et al. |
| 6,889,094 B1 | 5/2005 | Kuzma et al. |
| 6,909,917 B2 | 6/2005 | Woods et al. |
| 6,921,295 B2 | 7/2005 | Sommer |
| 6,922,591 B2 | 7/2005 | Single |
| 6,996,438 B1 | 2/2006 | Voelkel |
| 7,039,466 B1 | 5/2006 | Harrison et al. |
| 7,054,691 B1 | 5/2006 | Kuzma |
| 7,072,717 B1 | 7/2006 | Wolf et al. |
| 7,076,308 B1 | 7/2006 | Overstreet et al. |
| 7,082,332 B2 | 7/2006 | Blamey et al. |
| 7,085,605 B2 | 8/2006 | Bluger et al. |
| 7,146,227 B2 | 12/2006 | Dadd et al. |
| 7,197,152 B2 | 3/2007 | Miller et al. |
| 7,204,799 B2 | 4/2007 | Miller, III et al. |
| 7,204,800 B2 | 4/2007 | Easter et al. |
| 7,214,179 B2 | 5/2007 | Miller et al. |
| 7,260,436 B2 | 8/2007 | Kilgore et al. |
| 7,354,394 B2 | 4/2008 | Slattery, III et al. |
| 7,489,793 B2 | 2/2009 | Miller, III et al. |
| 7,522,738 B2 | 4/2009 | Miller, III |
| 7,556,597 B2 | 7/2009 | Miller, III et al. |
| 7,775,964 B2 | 8/2010 | Miller, III |
| 7,822,479 B2 | 10/2010 | Stracener |
| 7,840,020 B1 | 11/2010 | Miller, III et al. |
| 7,844,329 B2 | 11/2010 | Chambers |
| 8,185,212 B2 | 5/2012 | Carbunaru et al. |
| 8,550,977 B2 | 10/2013 | Kasic, II et al. |
| 8,657,734 B2 | 2/2014 | Parker |
| 8,771,166 B2 | 7/2014 | Conn |
| 2002/0032401 A1 | 3/2002 | Fereira et al. |
| 2002/0076071 A1 | 6/2002 | Single |
| 2002/0124857 A1 | 9/2002 | Schroeppel |
| 2003/0031336 A1 | 2/2003 | Harrison et al. |
| 2003/0050680 A1* | 3/2003 | Gibson ............... A61N 1/3752 607/116 |
| 2003/0055311 A1 | 3/2003 | Neukermans et al. |
| 2003/0120327 A1 | 6/2003 | Tobritzhofer |
| 2003/0181956 A1 | 9/2003 | Duncan et al. |
| 2004/0059403 A1 | 3/2004 | Massullo |
| 2004/0133250 A1 | 7/2004 | Ball et al. |
| 2005/0004629 A1* | 1/2005 | Gibson ................. A61N 1/375 607/60 |
| 2005/0005421 A1 | 1/2005 | Wang et al. |
| 2005/0096561 A1 | 5/2005 | Conn et al. |
| 2005/0101832 A1 | 5/2005 | Miller, III et al. |
| 2005/0137664 A1 | 6/2005 | Sommer et al. |
| 2005/0234522 A1 | 10/2005 | Ley et al. |
| 2006/0040541 A1 | 2/2006 | Vaughn |
| 2006/0122664 A1 | 6/2006 | Sacha et al. |
| 2006/0183965 A1 | 8/2006 | Kasic, II et al. |
| 2007/0016267 A1 | 1/2007 | Griffin et al. |
| 2007/0167671 A1 | 7/2007 | Miller, III |
| 2007/0217640 A1 | 9/2007 | Maltan et al. |

(56) References Cited

U.S. PATENT DOCUMENTS

| | | |
|---|---|---|
| 2007/0280495 A1 | 12/2007 | Abolfathi |
| 2007/0282397 A1 | 12/2007 | Ball et al. |
| 2008/0009202 A1 | 1/2008 | Yang |
| 2008/0027515 A1 | 1/2008 | Harris et al. |
| 2008/0049953 A1 | 2/2008 | Harney et al. |
| 2008/0085023 A1 | 4/2008 | Kulkarni et al. |
| 2008/0132750 A1 | 6/2008 | Miller |
| 2008/0167516 A1 | 7/2008 | Jaeger et al. |
| 2008/0221641 A1* | 9/2008 | Hochmair ............... A61F 11/04 607/57 |
| 2008/0234539 A1 | 9/2008 | Slattery et al. |
| 2008/0243214 A1 | 10/2008 | Koblish |
| 2009/0163978 A1 | 6/2009 | Miller, III et al. |
| 2009/0187065 A1 | 7/2009 | Basinger |
| 2009/0187233 A1 | 7/2009 | Stracener |
| 2009/0283294 A1 | 11/2009 | Bukovnik |
| 2009/0287277 A1 | 11/2009 | Conn et al. |
| 2010/0032205 A1 | 2/2010 | Williams |
| 2010/0256693 A1 | 10/2010 | McDonald |
| 2010/0272287 A1 | 10/2010 | Miller, III |
| 2010/0317913 A1 | 12/2010 | Conn et al. |
| 2011/0034755 A1 | 2/2011 | Parker |
| 2011/0178575 A1 | 7/2011 | Cryer |
| 2011/0218605 A1 | 9/2011 | Cryer |
| 2011/0264155 A1 | 10/2011 | Van den Heuvel et al. |
| 2011/0288614 A1 | 11/2011 | Cryer |
| 2012/0022647 A1* | 1/2012 | Leigh ..................... A61N 1/375 623/10 |
| 2012/0109297 A1 | 5/2012 | Van den Heuvel |
| 2013/0079844 A1 | 3/2013 | Conn et al. |
| 2014/0316190 A1 | 10/2014 | Conn et al. |
| 2014/0343626 A1* | 11/2014 | Thenuwara ............ A61N 1/375 607/57 |
| 2015/0367126 A1* | 12/2015 | Smyth .................. A61N 1/0541 607/137 |
| 2016/0008601 A1* | 1/2016 | Meadows ............ A61N 1/3752 607/59 |
| 2016/0235993 A1 | 8/2016 | Cryer |
| 2018/0028811 A1 | 2/2018 | Van Gerwen et al. |

FOREIGN PATENT DOCUMENTS

| | | |
|---|---|---|
| WO | WO2003101535 | 12/2003 |
| WO | 2004024212 A1 | 3/2004 |
| WO | WO2006062545 | 6/2006 |
| WO | 2006081361 A1 | 8/2006 |
| WO | WO2008089505 | 7/2008 |
| WO | 2009117767 A1 | 10/2009 |
| WO | WO2010028436 | 3/2010 |
| WO | 2010126996 A1 | 11/2010 |

OTHER PUBLICATIONS

W. West et al., "The Design of a Loud-Speaker," I.E.E. Wireless Proceedings, vol. 15, No. 44, Jun. 1940, pp. 4 and 54-67.

C. Gibbons et al., "Design of a Biomimetic Directional Microphone Diaphragm," Proceedings of International Mechanical Engineering Congress and Exposition, Nov. 5-10, 2000, Orlando, FL, pp. 1-7.

A. Rens Leeuw et al., "Advantages of Directional Hearing Aid Microphones Related to Room Acoustics," Audiology, Jan. 1991, 30: 330-344.

Specification sheet for beyerdynamic MCE 60 Condenser Microphone, pp. 1-2, accessible on line at http://northamerica.beyerdynamic.com/shop/mce-60-09-cable-with-free-ends-4.html, available Feb. 21, 2009.

* cited by examiner

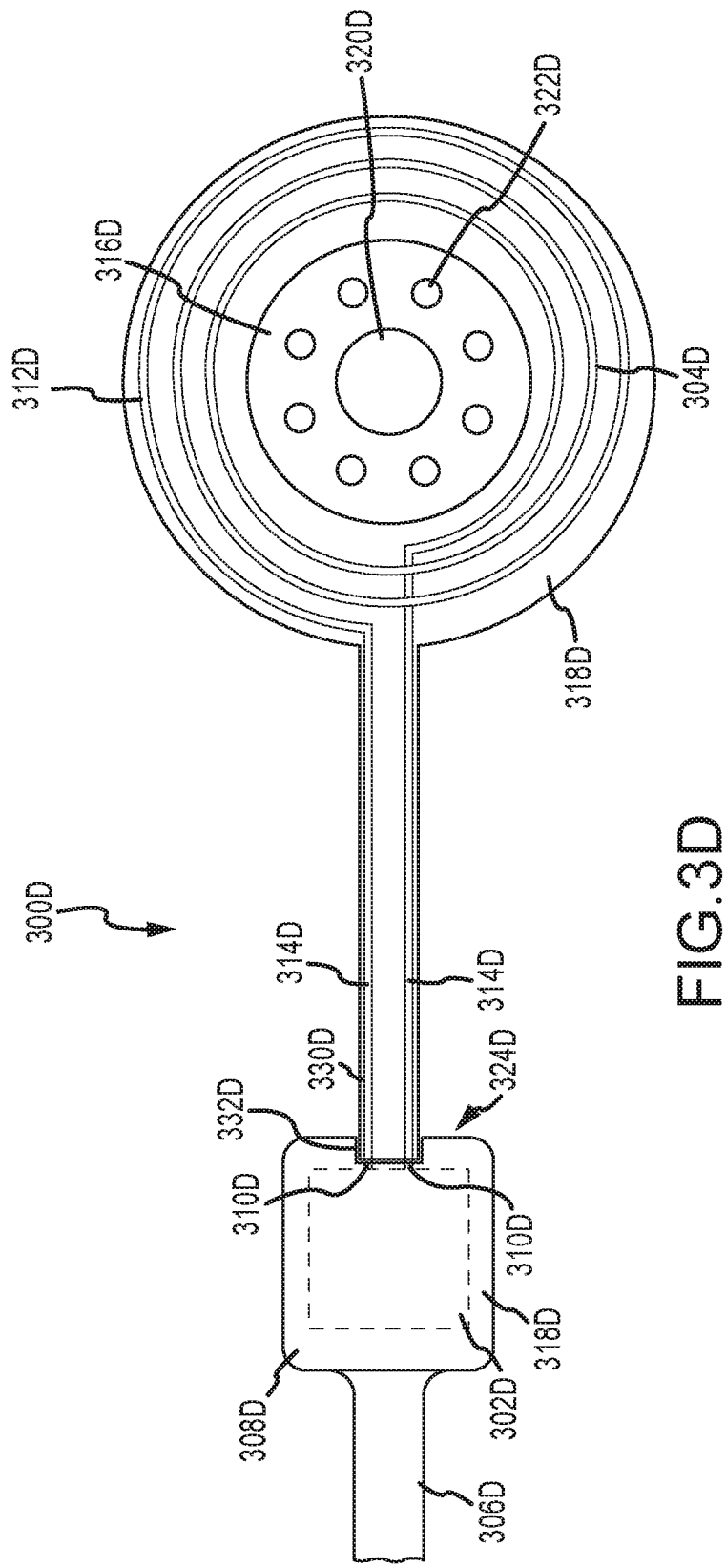

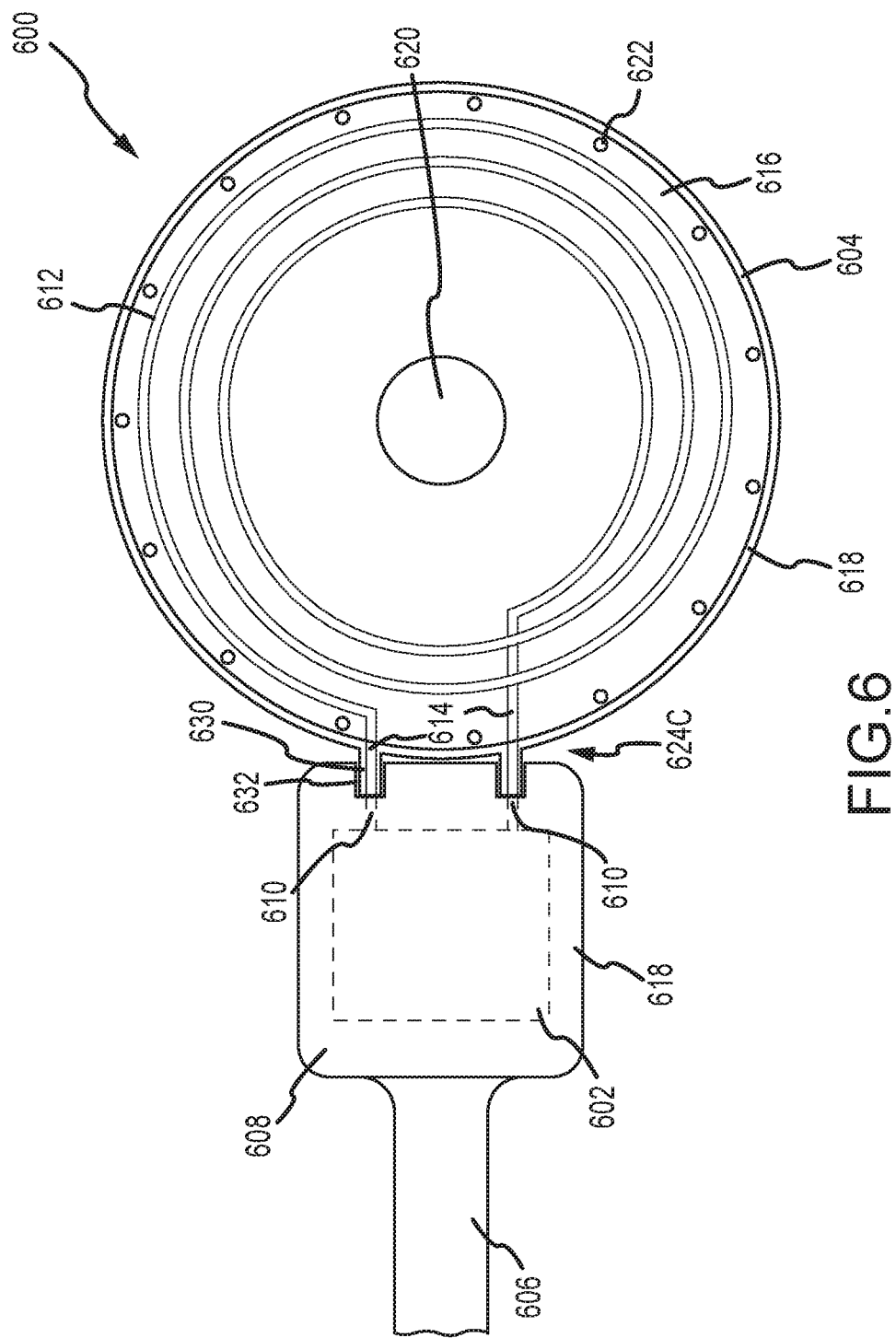

IMPLANTABLE DEVICE HAVING REMOVABLE PORTION

CROSS-REFERENCE TO RELATED APPLICATION

This application claims the benefit of U.S. Provisional Patent Application No. 62/299,467, filed Feb. 24, 2016, entitled "IMPLANTABLE DEVICE HAVING REMOVABLE PORTION", the disclosure of which is hereby incorporated by reference in its entirety herein.

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Implantable medical devices, such as auditory prostheses, often utilize an implanted component and an external component. Both components can include a magnet so as to hold the external component proximate the implanted component. The implanted magnet can interfere with MRI procedures. The medical devices described herein allow for the complete removal of a portion of the implantable component that contains the magnet.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

FIGS. 3A-3D are partial top views of implantable portions of cochlear implants in accordance with examples of the technology.

FIG. 6 is a partial top view of an implantable portion of a cochlear implant in accordance with another example of the technology.

DETAILED DESCRIPTION

The technologies described herein can typically be utilized with auditory prostheses such as cochlear implants. Such devices utilize one or more magnets disposed in an external portion of the cochlear implant. The magnetic field of this external magnet interacts with a magnetic field of a magnet disposed in an implanted portion of the cochlear implant. The technologies disclosed herein can have further application in other types of medical device implanted in a recipient. For example, other types of auditory prostheses, such as transcutaneous bone conduction devices, totally implantable cochlear implants, and direct acoustic stimulators utilize a similar configuration where a magnet is implanted below the skin of a recipient. Accordingly, the technologies described herein can be similarly leveraged in such devices. The technologies described herein can also be utilized in medical devices having certain components that can require removal (and replacement) at some point after implantation. For clarity, however, the technologies will be described in the context of cochlear implants.

One advantage to medical devices constructed in accordance with the following disclosure is that a portion of the device containing the magnet can be easily removed after implantation. This is particularly useful when a recipient of, e.g., a cochlear implant, must undergo an MRI procedure. A key issue in preforming MRI on a patient with an implanted medical device magnet is that the strong magnetic field applied by the MRI exerts a significant torque on the implanted magnet, regardless of magnet implantation location. For example, the torque exerted on a typical cochlear implant magnet in a 3T MRI machine is up to about 0.38 Nm. If the implanted magnet is inadequately constrained, the magnet can become dislodged, causing pain and potentially requiring surgery to correct. Another issue is that the magnet distorts the MRI magnetic field and causes a large image artifact. The image artifact for a cochlear implant with magnet is typically about 100 mm. As such, when imaging the head it can be very desirable to remove the magnet. In another example, the technologies described herein may be leveraged to allow for replacement of existing components (e.g., due to damage or failure) or as desired to upgrade certain components.

Figure 1:
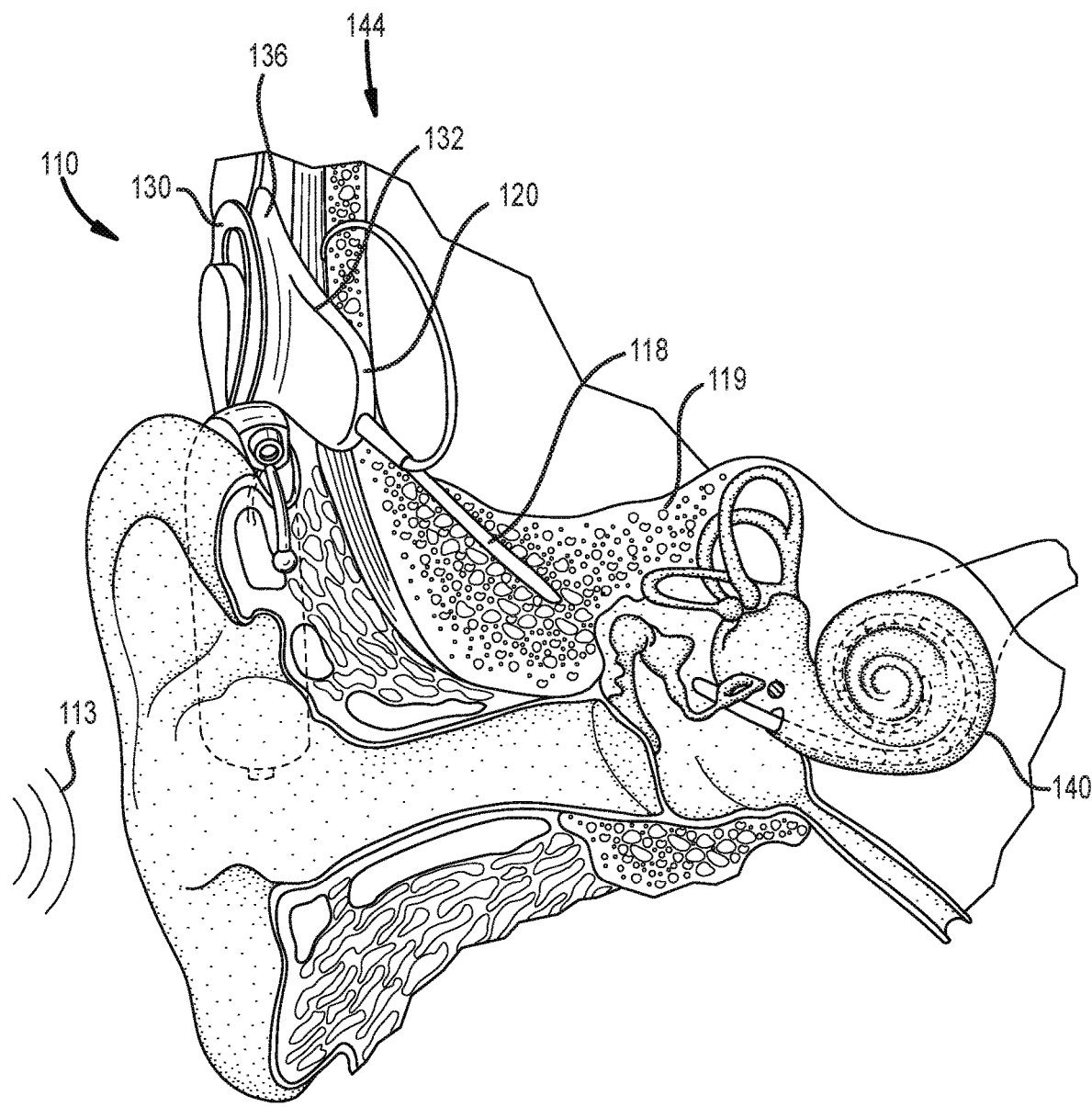
FIG. 1 is a partial view of a behind-the-ear auditory prosthesis worn on a recipient.

Referring to FIG. 1, cochlear implant system 100 includes an implantable component 144 typically having an internal receiver/transceiver unit 132, a stimulator unit 120, and an elongate lead 118. The internal receiver/transceiver unit 132 permits the cochlear implant system 110 to receive and/or transmit signals to an external device. The external device can be a button sound processor worn on the head that includes a receiver/transceiver coil and sound processing components. Alternatively, the external device can be just a receiver/transceiver coil in communication with a BTE device that includes the sound processing components and microphone. The implantable component 144 includes an internal coil 136, and preferably, a magnet (not shown) fixed relative to the internal coil 136. The magnet is embedded in a pliable silicone or other biocompatible encapsulant, along with the internal coil 136. Signals sent generally correspond to external sound 113. Internal receiver unit 132 and stimulator unit 120 are hermetically sealed within a biocompatible housing, sometimes collectively referred to as a stimulator/receiver unit. The magnets facilitate the operational alignment of the external and internal coils, enabling internal coil 136 to receive power and stimulation data from external coil 130. The external coil 130 is contained within an external portion. Elongate lead 118 has a proximal end connected to stimulator unit 120, and a distal end implanted in cochlea 140. Elongate lead 118 extends from stimulator unit 120 to cochlea 140 through mastoid bone 119.

In certain examples, external coil 130 transmits electrical signals (e.g., power and stimulation data) to internal coil 136 via a radio frequency (RF) link, as noted above. Internal coil 136 is typically a wire antenna coil comprised of multiple turns of electrically insulated single-strand or multi-strand platinum or gold wire. The electrical insulation of internal coil 136 is provided by a flexible silicone molding. Various types of energy transfer, such as infrared (IR), electromagnetic, capacitive and inductive transfer, can be used to transfer the power and/or data from external device to cochlear implant.

Figure 2:
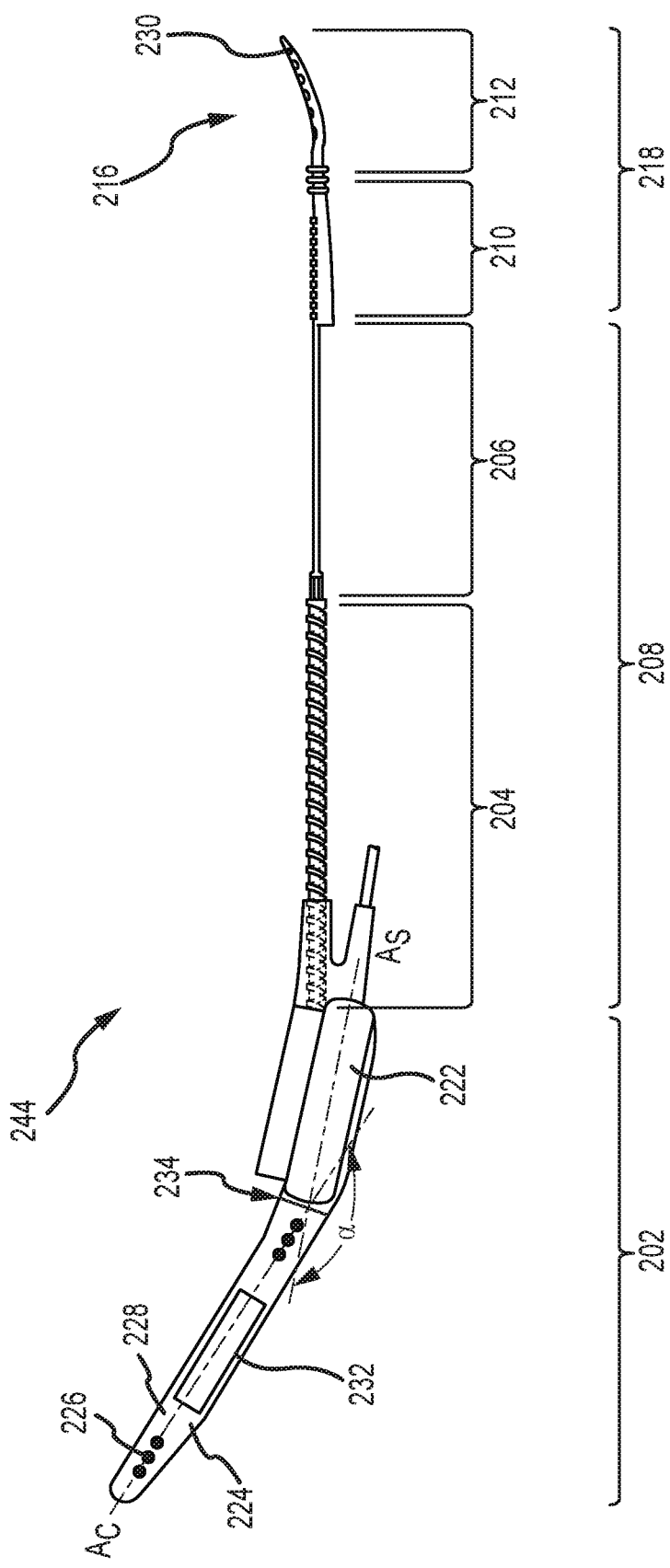
FIG. 2 is a side view of an example of an implantable portion of an auditory prosthesis.

FIG. 2 is a simplified side view of an internal component 244 having a stimulator/receiver unit 202 which receives encoded signals from an external component of the cochlear implant system. More specifically, the stimulator/receiver unit 202 includes an implantable stimulator unit or portion 222 and an implantable coil assembly or portion 224. Signals sent from an external sound processor (as described above) are received by a radio frequency induction coil 226 disposed within a polymer encapsulant 228 of the coil portion 224. The encapsulant 228 is a pliable biocompatible material (e.g., silicone) that displays flexibility sufficient to allow the coil assembly to substantially conform to the skull when implanted. A magnet chassis 232 is permanently embedded in the encapsulant 228 and contains therein a retention magnet (not shown). This magnet magnetically engages with an external magnet disposed on an external device that also includes a radio frequency induction coil. Signals, such as those corresponding to detected sound, are sent between the external coil and the implanted coil 226. These signals are processed by the stimulator unit 222 and sent as stimuli to the cochlear, via the remaining components of the internal component 244, as described below.

As described in detail elsewhere herein, the stimulator unit 222 and the coil portion 224 are releasably connected at an interface 234. The configuration of the connection elements at the interface 234 enables flexibility at the interface 234, which allows the stimulator/receiver unit 202 to more easily conform to the skull. The coil portion 224 defines a coil portion axis $A_C$, while the stimulator unit 222 defines a simulator unit axis $A_S$. Depending on the manufacturing details, connection element construction/orientation, material, or other factors, these axes $A_C$, $A_S$ can be substantially parallel or aligned or misaligned by a small angle, for example about 10 to about 15 degrees, prior to implantation. After implantation, however, the axes $A_C$, $A_S$ can deflect, such that an implantation angle α is formed by the axes $A_C$, $A_S$.

Internal component 244 terminates in a stimulating assembly 218 that comprises an extra-cochlear region 210 and an intra-cochlear region 212. Intra-cochlear region 212 is configured to be implanted in the recipient's cochlea and has disposed thereon a contact array 216. In the present example, contact array 216 comprises electrical contacts 230. The extra-cochlear region 210 and the intra-cochlear region 212 form a stimulating assembly 218.

Internal component 244 further comprises a lead region 208 coupling stimulator/receiver unit 202 to stimulating assembly 218. Lead region 208 comprises a region 204 which is commonly referred to as a helix region, however, the required property is that the lead accommodate movement and is flexible, it does not need to be formed from wire wound helically. Lead region also comprises a transition region 206 which connects helix region 204 to stimulating assembly 218. As described below, electrical stimulation signals generated by stimulator/receiver unit 202 are delivered to contact array 216 via lead region 208. Helix region 204 prevents lead region 208 and its connection to stimulator/receiver 202 and stimulating assembly 218 from being damaged due to movement of internal component 244 (or part of 244) which can occur, for example, during mastication.

Figure 3A:
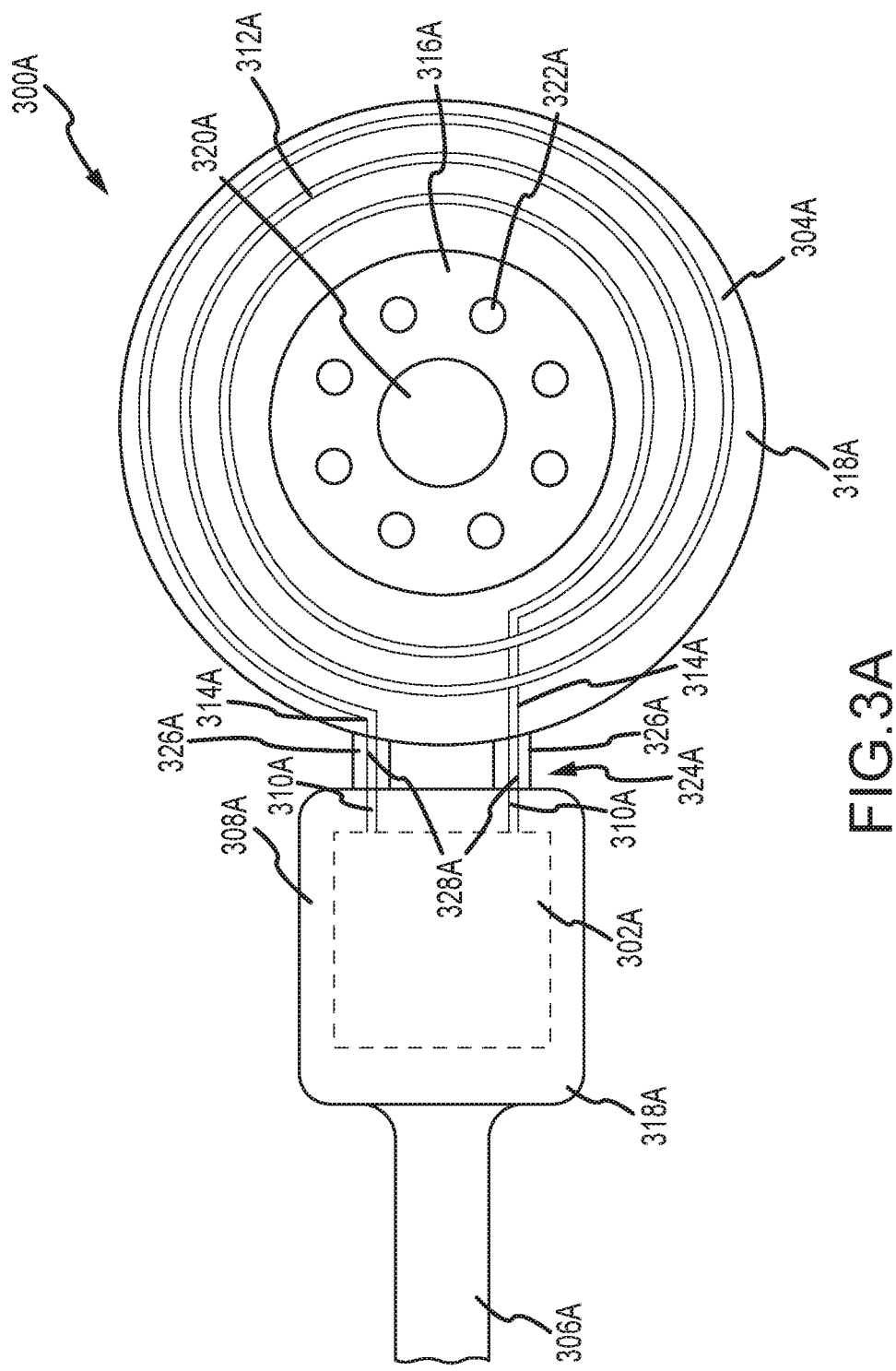
Figure 3B:
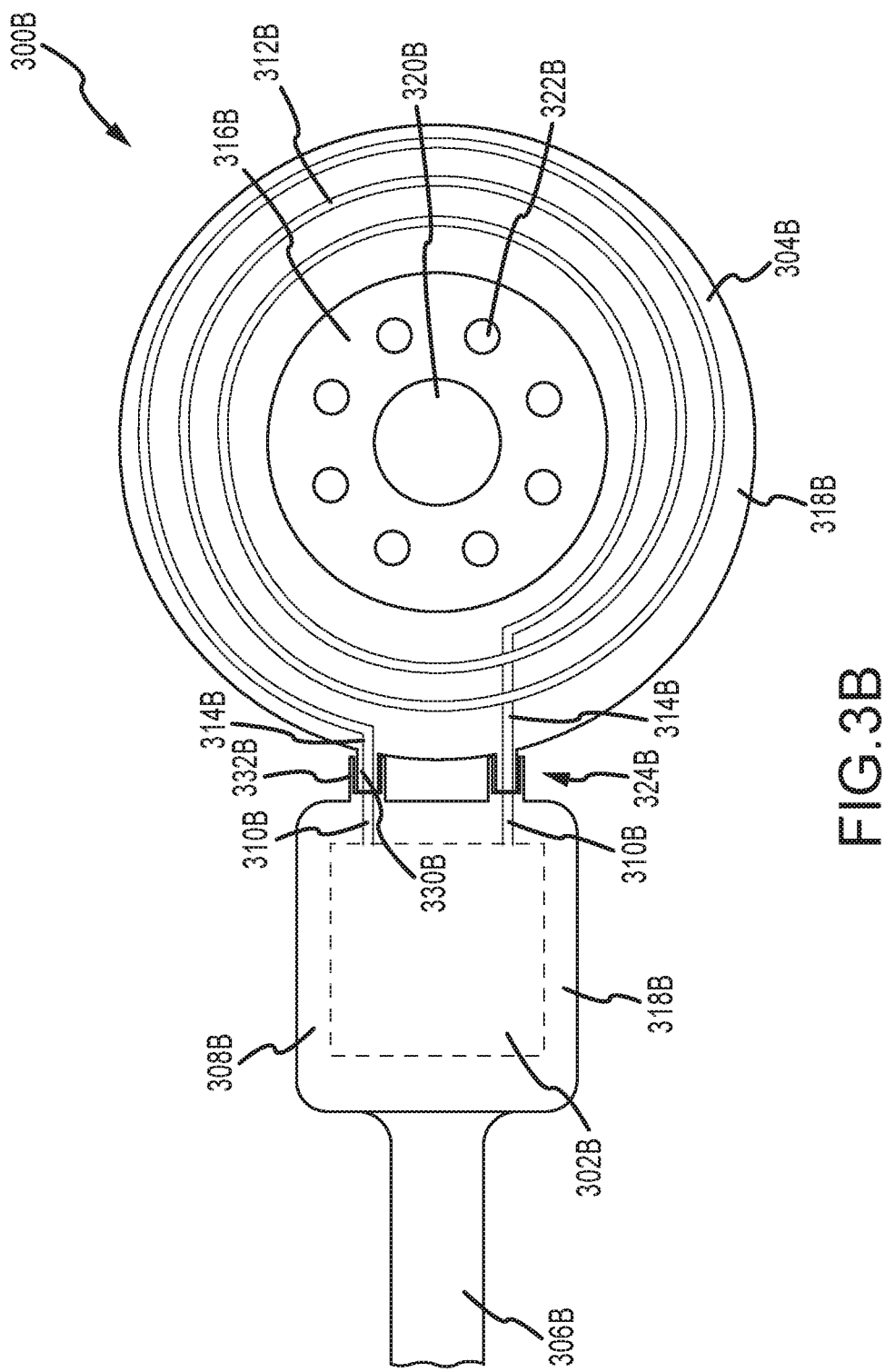
Figure 3C:
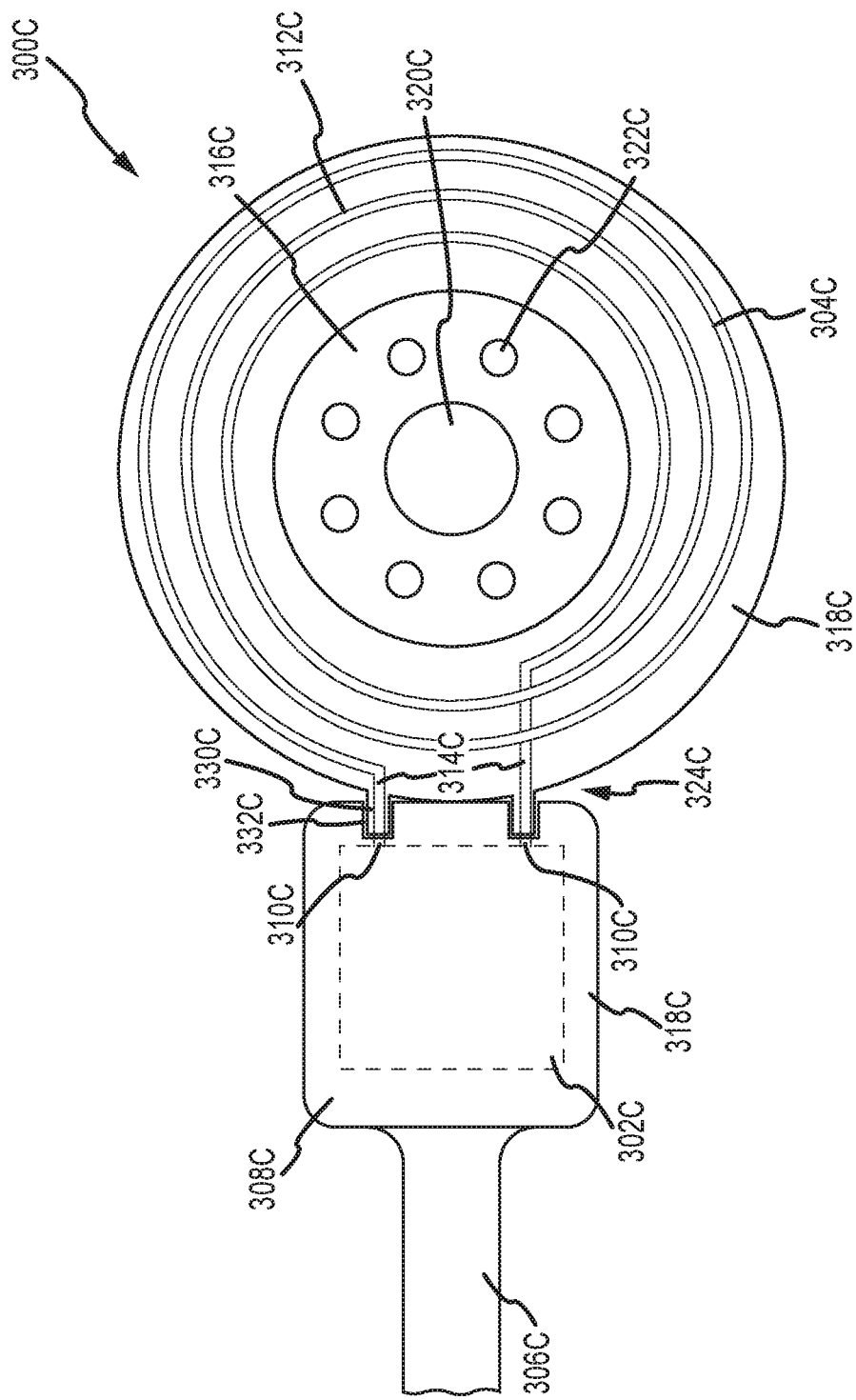

FIGS. 3A-3C are partial top views of implantable portions of cochlear implants 300A-D in accordance with examples of the technology and are generally described simultaneously. In general, the stimulator units 302A-D include electronics and a hermetic enclosure therearound, typically made of titanium, ceramic or a biocompatible polymer (such as PEEK), which encases the electronics of the stimulator units 302A-D. Coil assemblies or portions 304A-D are also depicted. A portion of helix regions 306A-D is depicted, but is described in further detail elsewhere herein. The hermetic enclosures containing the stimulator units 302A-D are encased in a pliable, biocompatible encapsulant 308A-D, such as silicone. Leads 310A-D are in electrical communication with the stimulator units 302A-D. The coil assemblies 304A-D include radio frequency induction coils 312A-D that are configured to wirelessly receive signals from an external portion of a cochlear implant, as described above. Leads 314A-D are in electrical communication with the induction coils 312A-D. Additionally, magnet chasses 316A-D are permanently embedded in the coil assemblies 304A-D, more specifically within the biocompatible polymer encapsulant 318A-D that forms a body of the coil assemblies 304A-D. The illustrated magnet chasses 316A-D include therein a number of through-holes 322A-D. Magnets 320A-D are disposed in the chasses 316A-D. One function of the through-holes 322A-D is described below. The stimulator units 302A-D and coil assemblies 304A-D are releasably connected at junctions or interfaces 324A-D at structures described generally as connectors, connector elements, or connector parts. These connectors releasably connect the stimulator units 302A-D to the coil assemblies 304A-D. As such, when connected via the connectors, the stimulator units 302A-D are in electrical communication with the coil assemblies 304A-D, can receive signals sent therefrom, and can send stimuli corresponding to such signals to the recipient. Various connectors, connection elements, or connector parts disposed at these interfaces 324A-D, are described below. These are but examples depicted to illustrate potential embodiments and generally describe the structures and advantages thereof. Other connectors are depicted and described in U.S. Pat. Nos. 7,844,329; 7,822,479; and 6,517,476, the disclosures of which are hereby incorporated by reference herein in their entireties. Connectors manufactured by Bal Seal Engineering, Inc., of Foothill Ranch, Calif., are also contemplated. In each of FIGS. 3A-3C, two connection elements are disposed at the interfaces 324A-C, but a single element can be used if required or desired.

In FIG. 3A, discrete connector elements or parts 326A are disposed at the interface 324A. The connector elements 326A each include a conductive path 328A that is coupled to both of the leads 310A, 314A. For example, the connector elements 326A can be sleeves or sheaths discrete from both the stimulator unit encapsulant 308A and the coil assembly encapsulant 318A. The conductive path 328A can be a conductive conduit or tube into which the leads 310A, 314A are inserted. In such a case, the conductive tube 328A can have an inner diameter slightly smaller than the outer diameter of the leads 310A, 314A. The tube 328A can form an interference fit with the leads 310A, 314A that is sufficient to hold them in place without damage to the leads 310A, 314A. Later removal of the leads 310A, 314A from the tube 328A can render the connector elements 326A unusable, thereby requiring new connector elements 326A, should reconnection of the stimulator unit 302A and coil assembly 304A be required or desired. In another example, the tube 328A can be crimped or deformed to as to be secured to the leads 310A, 314A.

FIG. 3B depicts a different connector structure at the interface 324B. Here, a male connector element or part 330B extends from and is optionally integral with the coil assembly encapsulant 318B. The leads 314B extend through the male connector element 330B. A mating female connector element or part 332B can extend from and be integral with the stimulation unit encapsulant 308B. Either or both of the male connector element 330B and the female connector element 332B can include one or more engaging tabs, detents, recesses, teeth, washers, or other retention elements that enable the male connector element 330B to be securely restrained within the female connector element 332B. Certain of these retention elements can provide tactile or audible feedback (e.g., a "click" sound) to ensure a proper connection.

FIG. 3C depicts a different connector structure at the interface 324C. Here, a male connector element or part 330C extends from and is optionally integral with the coil assembly encapsulant 318C. The leads 314C extend through the male connector element 330C. A mating female connector element or part 332C is formed within the stimulation unit encapsulant 308C. As with the example of FIG. 3B, either or both of the male connector element 330C and the female connector element 332C can include one or more engaging tabs, detents, recesses, teeth, washers, or other retention elements that enable to male connector element 330C to be securely restrained within the female connector element 332C. Certain of these retention elements can provide tactile or audible feedback to ensure a proper connection. The spacing between the stimulator unit 302C and coil assembly 304C (e.g., at the interface 324C) can be minimal in the configuration of FIG. 3C. This can help prevent the growth of biofilm at the interface 324C. Additional configurations to control or eliminate the growth of biofilm are known and can include the outer surfaces (upper, lower, perimeter, etc.) of the stimulator unit 302C and coil assembly 304C being formed with a smooth finish. Additionally, in configurations where the stimulator unit 302C and the coil assembly 304C abut each other, the abutments at the interfaces can be formed so as to reduce or eliminate discontinuities at the interface 324C that can cause biofilm to forms.

FIG. 3D depicts a different connector structure at the interface 324D. Here, a single male connector element or part 330D extends from and is optionally integral with the coil assembly encapsulant 318D. The leads 314D extend through the male connector element 330D. A mating female connector element or part 332D is formed within the stimulation unit encapsulant 308D. As above, either or both of the male connector element 330D and the female connector element 332D can include one or more engaging tabs, detents, recesses, teeth, washers, or other retention elements that enable to male connector element 330D to be securely restrained within the female connector element 332D. Certain of these retention elements can provide tactile or audible feedback to ensure a proper connection. The length of the male connector element 330D can be any length as required or desired for a particular application. This can help ease connection of the stimulator unit 302D and coil assembly 304D.

Figure 4:
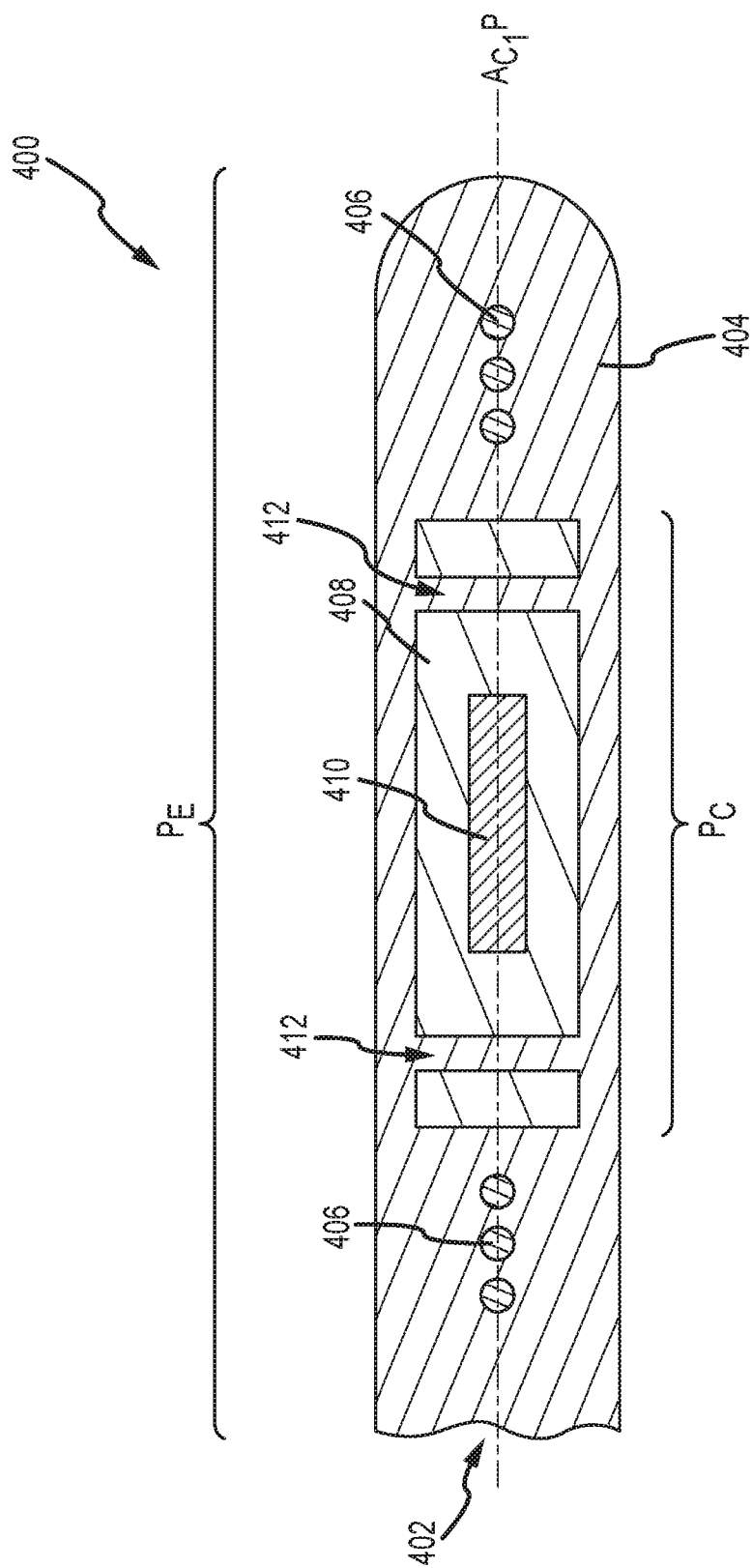
FIG. 4 is a partial side sectional view of an implantable coil assembly of a cochlear implant in accordance with an example of the technology.

FIG. 4 is a partial side sectional view of an implantable coil assembly 400 of a cochlear implant in accordance with an example of the technology. The interface 402 is depicted as a broken line, but connectors disposed thereon will be apparent to a person of skill in the art upon review of this disclosure. In relevant part, the implantable coil assembly 400 includes a body formed primarily of a polymer encapsulant 404. The encapsulant 404 permanently encases a radio frequency induction coil 406 and a magnet chassis 408 in which is disposed a magnet 410. The induction coil 406 defines a surface P along which all three of these elements 406, 408, 410 can be disposed. The surface P is generally planar and can incorporate a slight curvature to improve conformity with the shape of a recipient's skull. A coil assembly axis $A_C$ is generally parallel to or disposed within the surface P.

The magnet chassis 408 is formed of a material having a hardness greater than the hardness of the polymer encapsulant 404. For example, the polymer encapsulant can be silicone such as Nusil Med4860. The magnet chassis 408 can be formed of polyether ether ketone (PEEK), polyphenylsulfone (PPSU), or other rigid plastics. As with other implanted medical devices, it can be desirable that both the chassis 406 and encapsulant 404 are biocompatible. Thickness of the polymer encapsulant 404 on upper and lower surfaces of the chassis can be between about 0.2 mm and about 0.3 mm. A thicker layer of encapsulant can be applied to the lower surface of the chassis to the improve the magnet assembly's adaption to skull curvature.

The illustrated chassis 408 defines a number of through holes 412 that act as conduits into which the polymer encapsulant 404 enters during manufacture of the coil assembly 400. This can improve the mechanical linkage between the encapsulant 404 and the chassis 408. The through holes 412 are depicted as round, but any configuration can be utilized. Additionally or alternatively, other features around the edge of the chassis 408 (e.g., crenellations, serrations, etc.) can be utilized to engage with the polymer encapsulant 404.

The size and configuration of the magnet chassis 408 and its mechanical linkage to the encapsulant 404 helps the magnet chassis 408 resist rotational forces imposed thereon when the magnet 410 is disposed in a magnetic field (e.g., when the recipient is subject to an MRI procedure). In an example, the polymer encapsulant 404 of the body has a generally planar surface area $P_E$ parallel to the skull that is at least about 1.5 times greater than the corresponding surface area $P_C$ of the magnet chassis 408, which in turn has a surface area at least about 3 times greater than the magnet 410. In examples, depending on the surface areas of the various components, the body has a generally planar surface area $P_E$ that is at least about 2.2 times greater than a corresponding surface area $P_C$ of the magnet chassis 408 and over about 6 times greater than that of the magnet 410. As such, a torque resistance of the magnet chassis 408 and encapsulant 404 orthogonal to the plane of the coil 406 can be at least about 1.5 times greater than a corresponding torque resistance of the magnet 410 alone.

Depending on the particular configuration, torque resistance of the magnet chassis 408 can be 2-5 times greater than the torque resistance of the magnet 410 alone. This is because the magnet chassis 408 acts as an enlarged lever arm that resists rotation of the magnet 410. The larger magnet chassis 408 effectively increases the effective planar size of the magnet 410 (with regard to torque resistance), without actually increasing the physical size of the magnet 410 (with regard to torque generated thereon in a magnetic field). Coil assemblies 400 having configurations such as those depicted can resist torque generated by magnet fields up to about 1.5 T, with little discomfort or risk to the recipient. This configuration can also resist torque generated by magnetic fields up to about 3 T. The coil assembly 400 can be sized and configured such that higher magnetic fields can be resisted. Additionally, the coil assembly 400 can be disconnectable from the stimulator unit, as described elsewhere herein, so as to improve image quality or reduce discomfort.

Figure 5A:
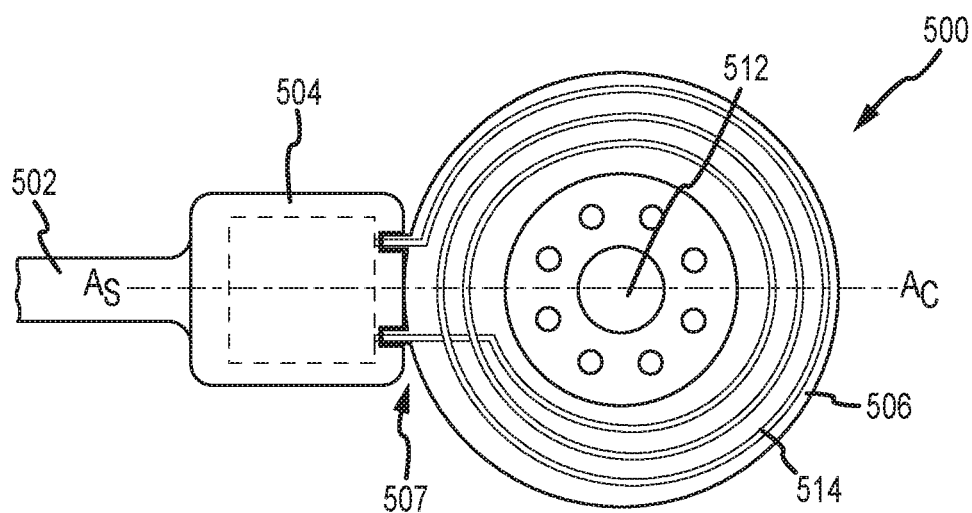
FIGS. 5A-5C depict a method of disconnecting an implantable coil assembly to an implantable stimulator unit, in vivo.
Figure 5B:
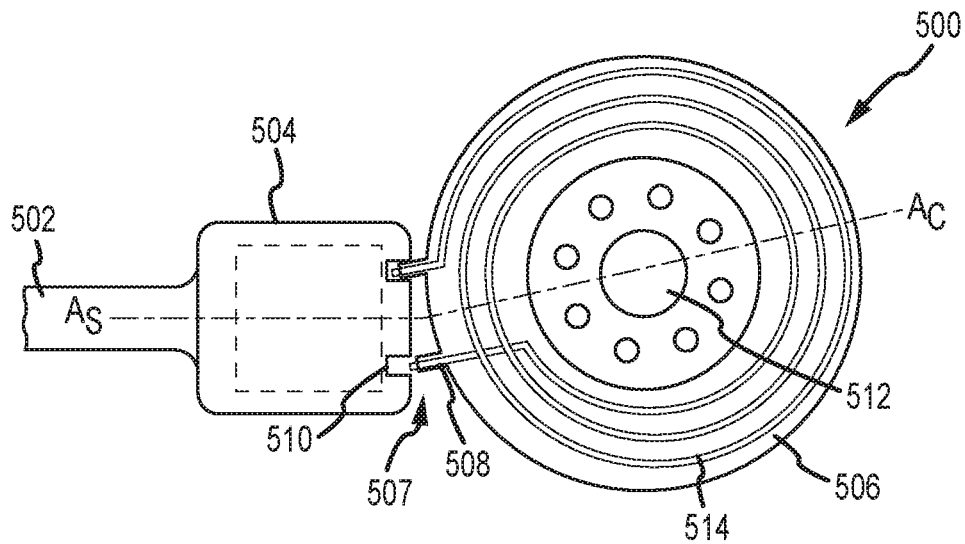
Figure 5C:
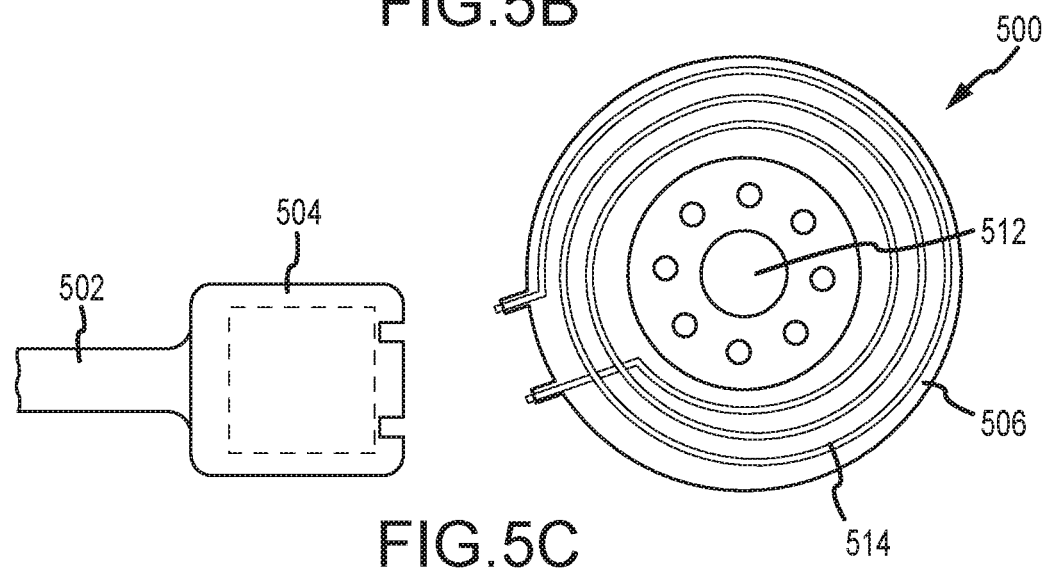

FIGS. 5A-5C depict a method of disconnecting components of a cochlear implant 500, in vivo. More specifically, the cochlear implant 500 includes a helix region 502, implantable stimulator unit 504, and an implantable coil assembly 506. In FIGS. 5A-5C, a portion of the helix region 502 is depicted, but not described, and the implantable stimulator unit 504 is implanted in a recipient. In FIG. 5A, the coil assembly 506 is connected to the stimulator unit 504 at the interface 507. Here, the stimulator unit axis $A_S$ and the coil assembly axis $A_C$ are substantially aligned. In FIG. 5B, disconnection of the coil assembly 506 from the stimulator unit 504 begins. After forming an incision in the head of the recipient, a surgeon can twist the coil assembly 506 relative to the stimulator unit 504 so as to misalign the axes $A_S$, $A_C$. Once sufficiently misaligned, the male and female connectors 508, 510 begin to disconnect. Once disconnected, as depicted in FIG. 5C, the stimulator unit 504 enters an MRI compatibility mode, where operation of the stimulator unit 504 ceases and wherein, due to removal of the coil assembly 506 (more specifically the magnet 512 therein), patient comfort and reduced artifacts are ensured. A controller within the stimulator unit 504 can include a physical or electronic switch that can automatically shut down the stimulator unit 504 and open the circuit or circuits associated with the stimulating electrodes (described elsewhere herein), thus preventing stimuli from being sent to the recipient. As such, the cochlear implant 500 is now in an MRI compatibility mode and the recipient can undergo an MRI procedure, at any field strength. The surgeon can cap or otherwise isolate the female connectors 510, then close the incision. Once the procedure is complete, the surgeon can re-open the incision and re-connect the coil assembly 506 in the reverse order (FIGS. 5C-5A).

Alternatively, a so-called "dummy coil assembly" can be connected to the stimulator unit 504. The dummy coil assembly has a form factor substantially similar to the coil assembly 506, includes a coil 514, but lacks a magnet 512. Such a component can be desirable because it enables the recipient to still receive sound stimuli, even if she is undergoing prolonged or multiple MRI procedures. As such, the coil assembly 506 and the dummy coil assembly are both selectively releasably connectable to the stimulator unit 504. Once connected, the coil of the dummy coil assembly is in communication with the stimulator unit 504. An external portion of the cochlear implant 500 containing an external coil can then be secured to the head (e.g., with an adhesive, headband, or other non-magnetic component) and signals can be sent between the two coils, as per normal operation. Once the MRI procedures are complete, the coil assembly 506 containing a magnet 512 can be re-connected and the device used normally.

FIG. 6 is a partial top view of an implantable portion of a cochlear implant 600 in accordance with another example of the technology. The stimulator unit 602 includes electronics and a hermetic enclosure therearound. A coil assembly or portion 604, as well as a portion of a helix region 606 are also depicted. The hermetic enclosure is encased in a pliable, biocompatible encapsulant 608. The coil assembly 604 includes a radio frequency induction coil 612 and leads 614 that are in communication with the stimulator unit 602 via leads 610. A magnet chassis 616 is permanently embedded in the coil assembly 604, more specifically within the biocompatible polymer encapsulant 618 that forms a body of the coil assembly 604. As with other examples described herein, the magnet chassis 616 can include therein a number of through-holes 622, as well as a magnet 620. The stimulator unit 602 and coil assembly 604 are releasably connected at junctions or interfaces 624 at structures described generally as connectors, connector elements, or connector parts. These connectors releasably connect the stimulator units 602 to the coil assemblies 604. Examples of such connectors are described elsewhere herein, but the depicted example utilizes a configuration similar to that depicted and described in FIG. 3C. As such, the interface 624 is not described further. Notably, in this example, the magnet chassis 616 has a diameter nearly the same as that of the outer perimeter of the coil encapsulant 618. As such, the coil 612 and magnet chassis 616 overlap. The coil 612 can be embedded within the chassis 616, along with the magnet 620, or overlay the skin facing surface of the magnet chassis 616, between the chassis 616 and encapsulant 618. This larger magnet chassis 616 further increases the size of the lever arm that opposes forces generated by a magnetic field, e.g., during an MRI procedure. Chasses having other diameters are contemplated. For example, chasses can have diameters slightly smaller than the smallest diameter of the coil. In such an example, the coil may be wrapped tightly about the outer perimeter of the chassis. For a larger chassis, it can be desirable that the underside of the chassis has a slight concave curvature, so as to rest more evenly on the surface of the skull.

Figure 7:
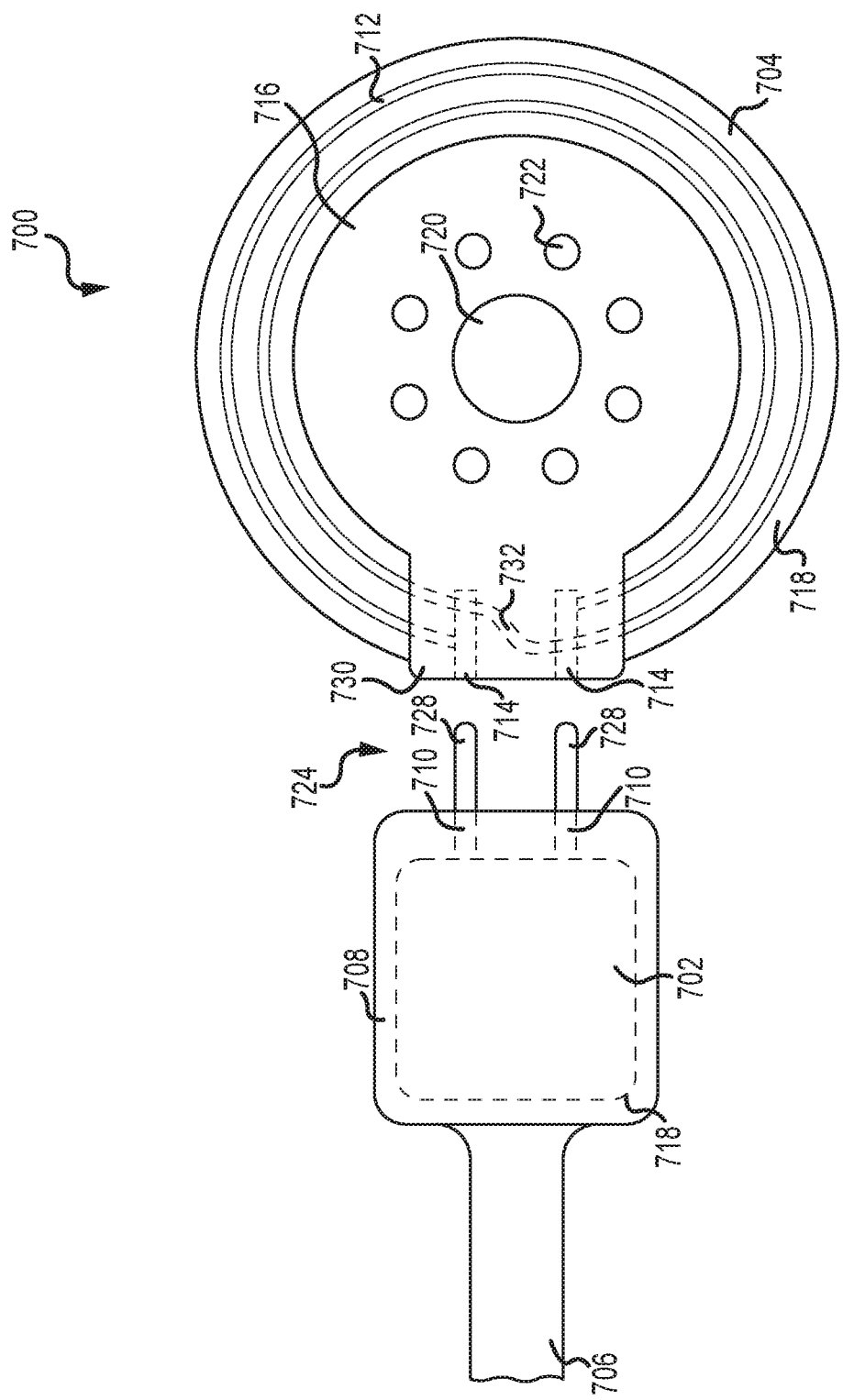
FIG. 7 is a partial top view of an implantable portion of a cochlear implant in accordance with another example of the technology.

FIG. 7 is a partial top view of an implantable portion of a cochlear implant 700 in accordance with another example of the technology. A stimulator unit 702 includes electronics and a hermetic enclosure therearound, typically made of titanium, ceramic or a biocompatible polymer (such as PEEK), which encases the electronics of the stimulator unit 702. A coil assembly 704 and a portion of a helix region 706 are also depicted. The hermetic enclosure containing the stimulator unit 702 is encased in a pliable, biocompatible encapsulant 708, such as silicone. Leads 710 are in electrical communication with and extend from the stimulator unit 702. In this example, the leads 710 connect to one or more conductive male prongs 728 that extend from the encapsulant 708. The coil assembly 704 includes a radio frequency induction coil 712 that, in the depicted example, is in a two-turn configuration. The induction coil 712 is configured to wirelessly receive signals from an external portion of a cochlear implant, as described above. Conductive sleeves, pockets, or receivers 714 are formed in an extension 730 of a magnet chassis 716 and are in electrical communication with the induction coil 712. More particularly, the extension 730 provides a rigid body into which the prongs 728 may be securely inserted, so as to form a positive connection to the coil assembly 704. The extension 730 may be completely encased in a biocompatible polymer encapsulant 718 or, as depicted, may extend slightly therefrom. As such, the magnet chassis 716 and extension 730 should be manufactured of a biocompatible material, if any portion thereof is disposed outside of the encapsulant 718.

As with the examples depicted above, the magnet chassis 716 include therein a number of through-holes 722 and a magnet 720 is disposed in the chassis 716. The stimulator unit 702 and coil assembly 704 are releasable connected at an interface 724 that may be defined at least in part by the exposed chassis extension 730. A biocompatible gasket or seal (not shown) may be disposed at the interface 724 between the prongs 728 and the chassis extension 730, so as to prevent the ingress of fluids into receivers 730 or into contact with the prongs 728, which may cause short-circuiting, interference, or other performance problems. Each conductive receiver 714 may form an interference fit with an associated conductive prong 728. In an example, this interference fit may be formed by a smaller diameter receiver 714 and a larger diameter prong 728. In another example, the interference fit may be formed by a resilient element disposed in the receiver 714 or on the prong 728. This resilient element may be an O-ring, tine or toothed element, or other structure. This interference may be overcome by a sufficient application of force to separate the stimulator unit 702 from the coil assembly 704.

In FIG. 7, a portion 732 of the induction coil 712 is routed through the chassis extension 730. This portion 732 may be disposed in a channel having a diameter larger than an outer diameter of the induction coil 712 material. This would allow for a movement of the induction coil within the chassis extension 730. Such movement may be desirable since the biocompatible polymer encapsulant 718 is more flexible than the chassis 716. Movement of the encapsulant 718 moves the coil 712, which could cause stress points on the coil 712 where the coil penetrates the chassis extension 730, potentially leading to failure thereof. By locating the portion 732 of the coil 712 within a larger channel, such stress points may be reduced or eliminated.

Figure 8A:
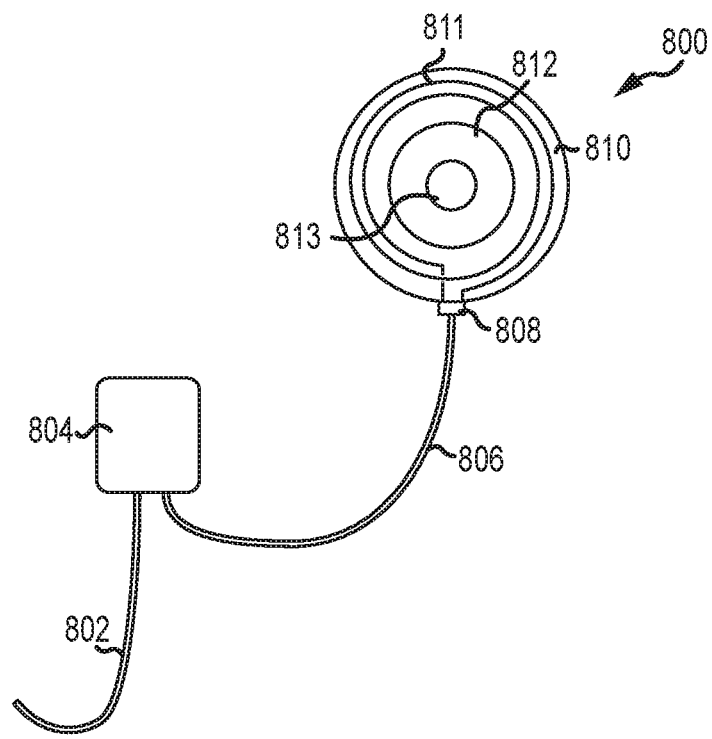
FIGS. 8A and 8B are examples of implantable auditory prostheses.
Figure 8B:
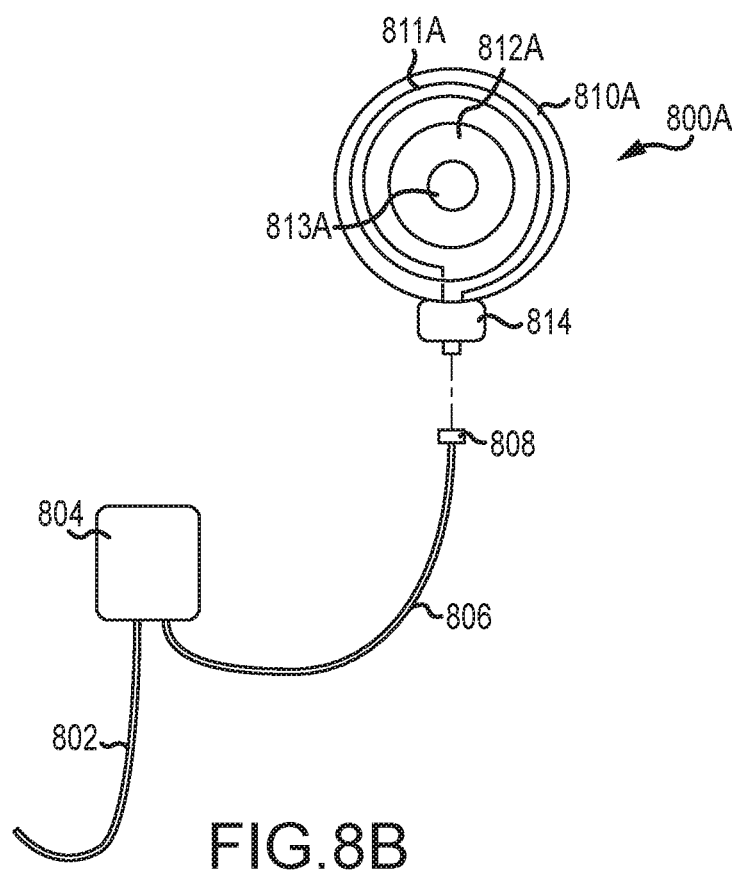

Other advantages of disconnectable components of a cochlear implant are contemplated and will also be apparent to a person of skill in the art. For example, a coil assembly having a more powerful magnet can replace a coil assembly having a weaker magnet. In another example, the coil assembly can operate as an upgrade pathway for the device. A coil assembly containing additional electronics, a battery, and/or an enhanced or more efficient coil can replace an initial coil assembly having none (or prior iterations) of those elements. An example of such an upgrade pathway is depicted in FIGS. 8A and 8B. FIG. 8A depicts a cochlear implant 800 including an electrode 802 and a stimulator unit 804 connected thereto. A lead 806 extends from the stimulator unit 804 and includes a connector 808 at a distal end thereof. In the various examples depicted above, the interfaces (the location where a coil assembly may be disconnected from an electrode) are depicted as a part of a stimulator unit that is, in turn, integral with the electrode. The connector technologies described herein, however, may also be used at the ends of leads that are permanently secured to the stimulator unit, as depicted in FIG. 8A. The depicted connector 808 may be a disconnectable component configured as in any of the configurations depicted herein (e.g., having mating components that enable disconnection of a coil assembly 810 from the connector 808). As described elsewhere herein, the coil assembly 810 may include a coil 811, a magnet chassis 812, and a magnet 813, as described in the various examples above.

By locating the connector 808 at the end of the flexible lead 806, the coil assembly 810 may be easily disconnected from the connector 808, with little or no movement of the electrode 808. As such, the possibility of dislocation of the electrode within, or trauma to, the cochlea may be reduced or eliminated. Once removed, the coil assembly 810 may be replaced with a different coil assembly (that is, e.g., having a stronger magnet, a different coil, or other feature or component). In the example depicted in FIG. 8B, however, the coil assembly 810 (from FIG. 8A) is replaced with an upgraded coil assembly 810A. The upgraded coil assembly 810A may include a coil 811A, a magnet 813A, and a magnet chassis 812A that may be similar to or different from those in the embodiment of FIG. 8A. The upgraded coil assembly 810A, however, also includes a module 814 that, when connected to the connector 808, forms an upgraded auditory prosthesis 800A. In an example, the auditory prosthesis 800 of FIG. 8A may be a cochlear implant that utilizes an external coil unit, sound processor, and microphone. The upgraded auditory prosthesis 800A may be a totally implantable cochlear implant. As such, the module 814 may include a sound processor, microphone, and other required or desired components. The upgraded coil assembly 810A is utilized with an external component to adjust settings of a totally implantable cochlear implant, as known in the art. As such, by utilizing the connector technologies described herein, a cochlear implant may be easily upgraded to a totally implantable cochlear implant, while reusing certain components that are common to both types of auditory prostheses (e.g., electrode 802, stimulator unit 804, and lead 806).

Figure 9:
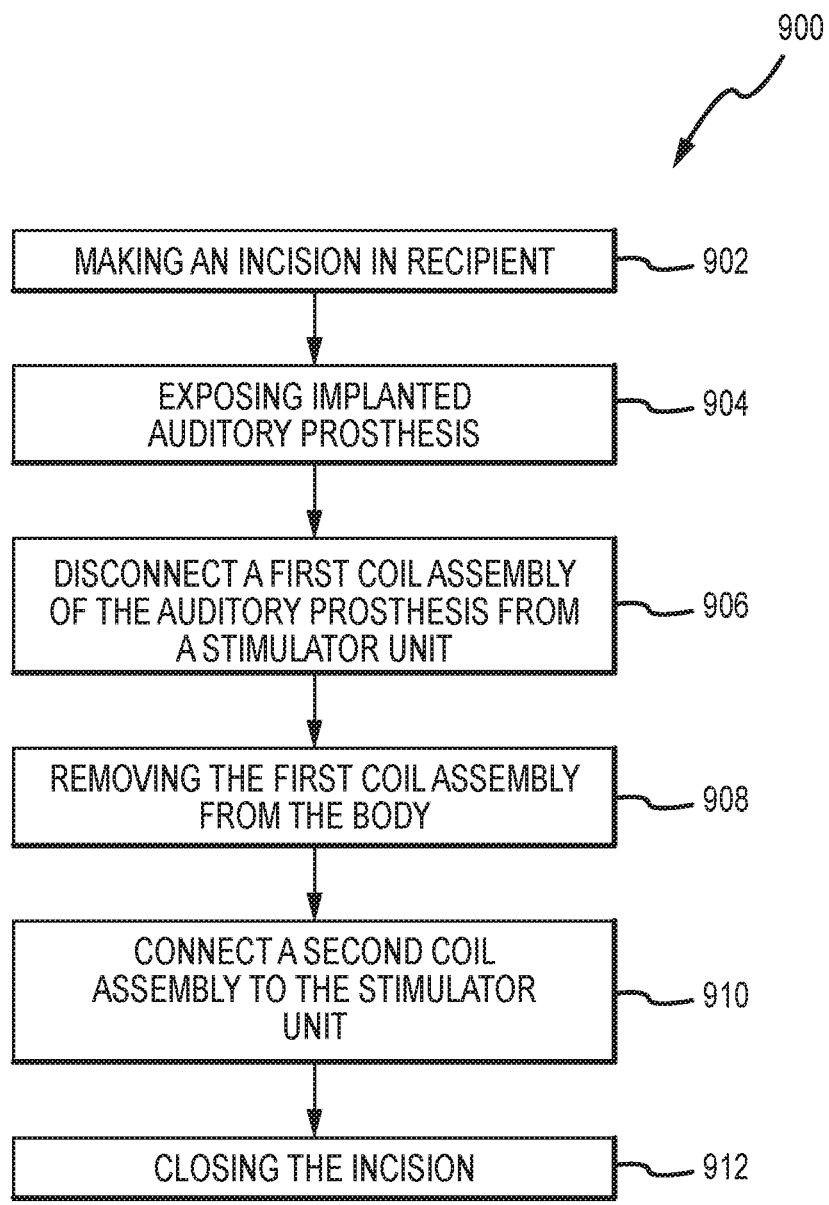
FIG. 9 depicts a method of replacing, in vivo, a portion of an implanted medical device.

FIG. 9 depicts a method 900 of replacing, in vivo, a component from an implanted medical device. The method 900 is described in the context of removing a coil assembly from an auditory prosthesis such as a cochlear implant. The method 900 can also be used to remove any type of component from a medical device, without having to remove the entire medical device from the body. The method 900 begins by making an incision in the implant recipient, operation 902. The skin can be withdrawn such that the incision exposes at least a portion of the cochlear implant, operation 904, typically a coil assembly. The coil assembly can be disconnected from the stimulator unit, consistent connector technologies described herein, in operation 906. As such, operation 906 contemplates disconnecting an electrical connection between the coil assembly and the stimulator unit upon disconnection of those two components. The disconnected portion (e.g., the coil assembly) is removed from the body in operation 908. A second component (e.g., a different coil assembly with a stronger or weaker magnet, or no magnet at all) is then connected to the stimulator unit in operation 910, thus re-forming the electrical connection between components. The second component can also be the same coil assembly initially removed. For example, the second component can be an identical, sterile coil assembly used to replace a damaged, non-sterile, or inoperable coil assembly. The incision is then closed at the conclusion of the method 900, in operation 914.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. An apparatus comprising:
   an implantable device comprising:
      a stimulator portion including a stimulator connector part;
      a first coil assembly including a first coil connector part releasably connectable to the stimulator connector part; and
      a controller configured to deactivate the stimulator portion when the first coil assembly is disconnected.

2. The apparatus of claim 1, wherein:
   the apparatus further comprises:
      a second coil assembly including a second coil connector part,
      wherein the stimulator connector part is selectively releasably connectable to both of the first coil connector part and the second coil connector part;
   the first coil assembly includes a first body and a first radio frequency induction coil embedded in the first body;
   the first radio frequency induction coil is electrically connected to the first coil connector part;
   the second coil assembly includes a second body and a second radio frequency induction coil embedded in the second body; and
   the second radio frequency induction coil is electrically connected to the second coil connector part.

3. The apparatus of claim 2, wherein the first coil assembly includes a first magnet configured to generate a first magnetic field, and wherein the second coil assembly includes a second magnet configured to generate a second magnetic field greater than the first magnetic field.

4. The apparatus of claim 1, further comprising an implantable power source.

5. The apparatus of claim 1, wherein the first coil assembly comprises:
   a pliable polymer encapsulant;
   a magnet; and
   a rigid magnet chassis that encases the magnet and is permanently embedded in the polymer encapsulant, wherein the chassis has through holes through which the polymer extends so that the chassis is improvedly mechanically linked to the polymer encapsulant beyond that which would be the case in the absence of the through holes.

6. The apparatus of claim 1, wherein the first coil assembly is twistable relative to the stimulator portion so as to misalign the first coil assembly relative to the stimulator portion so as to begin to disconnect the first coil connector part from the stimulator connector part.

7. An apparatus comprising:
   an implantable stimulator unit;
   an implantable power source;
   an implantable coil assembly configured to wirelessly couple the implantable stimulator unit with an external component of an auditory prosthesis; and
   a releasable connector disposed between the implantable coil assembly and the implantable stimulator unit, wherein the releasable connector is configured to electrically connect the implantable coil assembly to the implantable stimulator unit, wherein
   the apparatus is configured to deactivate the implantable stimulator unit when the implantable coil assembly is disconnected from the implantable stimulator unit.

8. The apparatus of claim 7, wherein:
   the implantable coil assembly comprises:
      a polymer encapsulant;
      a radio frequency coil permanently embedded in the polymer encapsulant;
      a magnet; and
      a magnet chassis that encases the magnet and is permanently embedded in the polymer encapsulant;
   the radio frequency coil is disposed in a plane, and the magnet and magnet chassis each have a major axis that is generally parallel with the plane of the radio frequency coil; and
   the magnet chassis has a surface area that is at least 3 times greater than a corresponding surface area of the magnet in the plane of the radio frequency coil.

9. The apparatus of claim 7, wherein:
   the implantable coil assembly comprises:
      a polymer encapsulant;
      a radio frequency coil permanently embedded in the polymer encapsulant;
      a magnet; and
      a magnet chassis that encases the magnet and is permanently embedded in the polymer encapsulant;
   the radio frequency coil is disposed in a plane, and the magnet and magnet chassis each have a major axis that is generally parallel with the plane of the radio frequency coil, wherein the magnet is in direct contact with the magnet chassis; and
   the magnet chassis has a torque resistance orthogonal to the plane of the radio frequency coil that is at least 1.5 times greater than the corresponding torque resistance of the magnet.

10. The apparatus of claim 7, wherein the implantable coil assembly and the implantable stimulator unit define a smooth upper surface and a smooth lower surface without substantial discontinuities at a junction between the implantable coil assembly and the implantable stimulator unit.

11. The apparatus of claim 7, wherein the releasable connector comprises a mechanical locking mechanism that secures the implantable coil assembly to the implantable stimulator unit and gives tactile feedback when an electrical connection is formed between the implantable coil assembly and the implantable stimulator unit.

12. The apparatus of claim 7, wherein:
the apparatus includes a controller electrically connected to the releasable connector and configured to deactivate the implantable stimulator unit when the implantable coil assembly is disconnected from the implantable stimulator unit;
the apparatus is a totally implantable cochlear implant; and
the apparatus is configured such that removing the implantable coil assembly causes the controller to enter an MRI compatibility state.

13. The apparatus of claim 7, further comprising:
a controller electrically connected to the releasable connector and configured to deactivate the implantable stimulator unit when the implantable coil assembly is disconnected from the implantable stimulator unit.

14. The apparatus of claim 7, wherein the releasable connector comprises an elongate male element that is arrayed with first electrical contacts along the longitudinal axis of the elongate male element and an elongate hollow portion that receives the elongate male element, the elongate hollow portion also arrayed with second electrical contacts that touch respective first electrical contacts when the elongate male element is fully seated in the hollow portion.

15. The apparatus of claim 7, wherein a second portion of the apparatus that includes the implantable coil has a rigid body into which a male portion of a first portion of the apparatus that includes the implantable stimulator unit is securely inserted, the rigid body and the male portion establishing the releasable connector, and wherein the rigid body is an extension of a magnet chassis that houses a magnet and is encapsulated in an encapsulant, the apparatus including the magnet and the magnet chassis and the encapsulant.

16. The apparatus of claim 7, wherein the implantable coil assembly comprises:
an encapsulant;
a radio frequency coil permanently embedded in the encapsulant;
a magnet; and
a magnet chassis that encases the magnet and is embedded in the encapsulant, wherein the magnet chassis has a diameter nearly the same as that of an outer perimeter of the encapsulant, wherein the radio frequency coil and the magnet chassis overlap when viewed from the top of the apparatus.

17. An apparatus comprising:
an implantable stimulator unit;
an electrode array including stimulating electrodes in signal communication with the implantable stimulator unit;
an implantable coil assembly configured to wirelessly couple the implantable stimulator unit with an external component of an auditory prosthesis, the implantable coil assembly in signal communication with the implantable stimulator unit; and
a controller within the implantable stimulator unit including a physical and/or electronic switch that can automatically shut down the implantable stimulator unit and/or open a circuit or circuits associated with the stimulating electrodes, thus preventing stimuli from being sent to the recipient of the implantable stimulator unit.

18. The apparatus of claim 17, wherein:
the implantable coil assembly lacks a magnet within the coil.

19. An apparatus comprising:
an implantable stimulator unit;
an electrode array including stimulating electrodes in signal communication with the implantable stimulator unit;
an implantable coil assembly configured to wirelessly couple the implantable stimulator unit with an external component of an auditory prosthesis, the coil in signal communication with the implantable stimulator unit; and
a controller within the implantable stimulator unit including a physical and/or electronic switch that can automatically shut down the implantable stimulator unit, thus preventing stimuli from being sent to a recipient of the implantable stimulator unit.

* * * * *